(12) United States Patent
Jaroszeski et al.

(10) Patent No.: US 8,348,942 B1
(45) Date of Patent: Jan. 8, 2013

(54) DEVICE AND METHOD TO PREVENT HAIR GROWTH

(75) Inventors: Mark J. Jaroszeski, Wesley Chapel, FL (US); Gabriel A. Lopez-Diaz, Wesley Chapel, FL (US); Richard J. Connolly, Riverview, FL (US); Andrew M. Hoff, Tampa, FL (US)

(73) Assignee: University of South Florida, Tampa, FL (US)

( * ) Notice: Subject to any disclaimer, the term of this patent is extended or adjusted under 35 U.S.C. 154(b) by 685 days.

(21) Appl. No.: 12/559,892

(22) Filed: Sep. 15, 2009

Related U.S. Application Data

(60) Provisional application No. 61/096,994, filed on Sep. 15, 2008.

(51) Int. Cl.
*A61B 18/18* (2006.01)
(52) U.S. Cl. ............................................ 606/43; 606/36
(58) Field of Classification Search ................ 606/36–43
See application file for complete search history.

(56) References Cited

U.S. PATENT DOCUMENTS

| | | | |
|---|---|---|---|
| 4,040,426 A * | 8/1977 | Morrison, Jr. ................... | 606/49 |
| 4,498,474 A | 2/1985 | Chalmers et al. | |
| 4,781,175 A * | 11/1988 | McGreevy et al. ............. | 606/40 |
| 6,168,590 B1 | 1/2001 | Neev | |
| 6,407,056 B1 | 6/2002 | Seiberg et al. | |
| 6,575,969 B1 * | 6/2003 | Rittman et al. ................. | 606/41 |
| 7,186,234 B2 | 3/2007 | Dahla et al. | |
| 7,316,682 B2 * | 1/2008 | Konesky ......................... | 606/40 |
| 7,572,255 B2 * | 8/2009 | Sartor et al. .................... | 606/41 |
| 7,691,102 B2 * | 4/2010 | Podhajsky et al. .............. | 606/41 |
| 2003/0084907 A1 | 5/2003 | Pacek et al. | |
| 2006/0189976 A1 | 8/2006 | Karni et al. | |

OTHER PUBLICATIONS http://www.valleylab.com/education/poes/poes_02.html. Principles of Electrosurgery : Electrocautery. Accessed on Sep. 6, 2012.
http://www.valleylab.com/education/poes/poes_03.html. Principles of Electrosurgery : Principles of Electrosurgery in the OR. Accessed on Sep. 6, 2012.

* cited by examiner

*Primary Examiner* — Linda Dvorak
*Assistant Examiner* — Amanda Scott
(74) *Attorney, Agent, or Firm* — Michele L. Lawson; Jeremy Spier; Smith & Hopen, P.A.

(57) ABSTRACT

A device and method to cause hair loss or prevent or inhibit hair growth. The invention uses plasma (ionized gas) that is generated by flowing gas in close proximity to an electrode that has a high potential applied to it. The result is a stream of charged gas particles that are directed to the skin that contains hair. The flowing stream of gas is held above the surface of the skin. Additionally, a grounded conductive material is affixed to the skin to dissipate any charge buildup on the skin and focus the plasma.

20 Claims, 6 Drawing Sheets

DEVICE AND METHOD TO PREVENT HAIR GROWTH

CROSS-REFERENCE TO RELATED APPLICATIONS

This application claims priority to U.S. Provisional Patent Application No. 61/096,994, entitled "Device and Method to Prevent Hair Growth," filed on Sep. 15, 2008, which is herein incorporated by reference.

BACKGROUND OF THE INVENTION

1. Field of the Invention

This invention relates to a device and method to cause hair loss or prevent or inhibit hair growth. More specifically, the invention uses a stream of charged gas particles (i.e., plasma) that are directed to the skin that contains hair.

2. Description of the Prior Art

The principal methods presently used for inhibiting hair growth involve the use of lasers, electrolysis techniques, waxing, or chemical depilatories. These techniques involve some pain, can cause permanent damage to the skin, have high costs, are time consuming, and demand a fair degree of expertise in their application.

What is needed is a simple, safe, and cheap device and method for the removal of hair. However, in view of the prior art considered as a whole at the time the present invention was made, it was not obvious to those of ordinary skill in the art of hair removal how the identified needs could be met.

SUMMARY OF INVENTION

In view of the foregoing problems, the novel invention discloses a simple, harmless, and economical apparatus and method for the prevention of hair growth.

The method to cause hair loss or prevent or inhibit hair growth includes the steps of introducing a substantially continuous electric field, in the form of non-thermal plasma (i.e., ionized gas) generated by a DC voltage applied to an electrode, to the surface of a biological structure. Specifically, a DC voltage is applied to an electrode creating a first potential. A gas source supplies a stream of gas past the first potential creating a second potential, the second potential being either positive or negative plasma. The second potential is applied to a biological structure for the necessary time and at the necessary distance to achieve hair loss or inhibit/prevent growth. A means for controlling the flow of gas, run time, voltage, and current is provided. Multiple second potentials may be applied simultaneously or in series to expedite or improve the process. A conductive material that is grounded and in contact with the biological structure is used to dissipate any charge buildup and to focus the plasma to the target tissue.

The apparatus is a hollow body with a gas source in fluid communication. Gas enters the first end and exits the second end of the hollow body. The gas flow is controlled by a flowmeter. An electrode connected to a power supply is positioned at the second end of the hollow body. When the electrode is energized, an electric field is created. As the gas flows past the electric field, the gas becomes ionized (i.e., plasma). The plasma exits the hollow body and is directed to a biological source, resulting in hair growth prevention/inhibition or loss. A grounding device may be used in conjunction with the apparatus to dissipate any charge buildup. The grounding device is grounded and in electrical contact with the biological source. The grounding device may be connected to a material having high impedance. The voltage, current, and run time of the apparatus is controlled by computer interface program such as LabVIEW®. For accurate targeting, the hollow body has a pointing device attached to it and is mounted to a manipulator arm.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention. For example, charge from many sources can be applied to achieve the same effects. These can include but are not limited to: corona charge, DC plasma, AC plasma, RF plasma, plasma formed from any gas (including air), plasma formed from any mixture of two or more gasses, and electrospray technology.

The present invention includes a method and associated apparatus for the delivery of a potential which results in hair loss or prevents or inhibits hair growth. The method and apparatus in accordance with the present invention are effective in using an electrical field to adjust the potential of a target surface.

The plasma used in this invention is a nonthermal helium (He) plasma that is generated by passing high purity He through a conductive ring that is at a constant DC voltage. The resulting ionized gas (i.e., plasma) is directed by the He flow to the target tissue which is skin. It was determined in mouse skin that applying the plasma treatment to the shaved flanks of mice for different times completely stopped the regrowth of hair. Similar results were found when either a positive polarity electrode or negative polarity electrode were used to create the plasma. There was no physical contact between the plasma pen and the target tissue. In fact, the plasma generating device was several centimeters (0-20 cm) away from the skin during treatment. Further, there was no observed stimulation of muscles in the mice. This was due to the fact that the He plasma treatment supplied very low levels of current (microamps).

Figure 1:
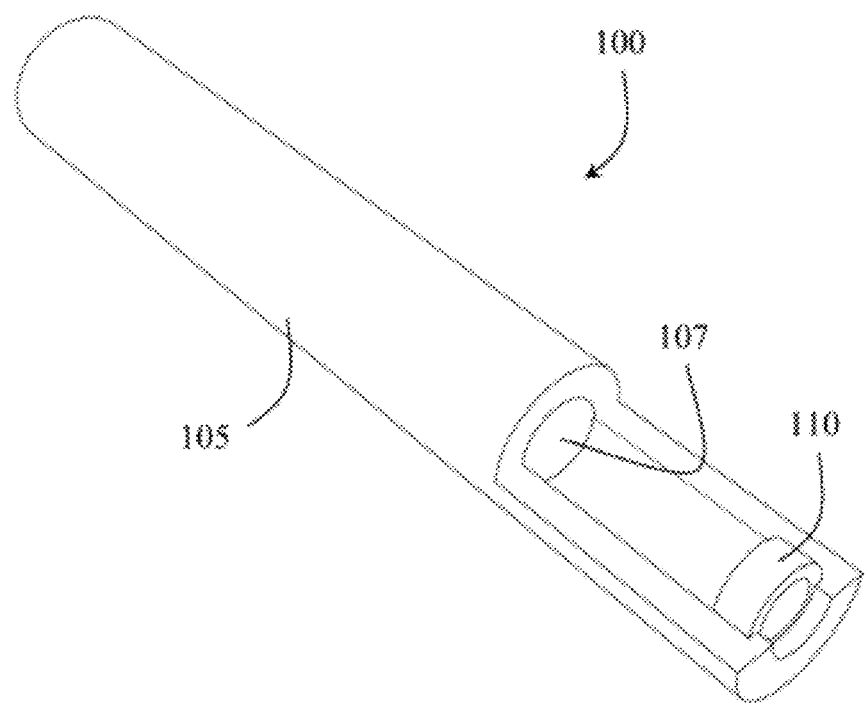
FIG. 1 is a perspective view of the plasma pen.

Referring now to FIG. 1, electric field generation device 100 includes tube 105 having inner channel 107. Tube 105 is approximately 15 cm long and the diameter of inner channel 107 is approximately 1 cm. Annular electrode 110 is positioned substantially at the opening of tube 105. Tube 105 is connected to a high-voltage and low-current direct current power supply. In this embodiment, an electric potential of about +8 kV or −8 kV is applied to electrode 110 depending on the desired polarity. A stream of ultra high purity helium is passed through inner channel 107 and electrode 110 at a rate of 15 l/min.

Figure 2:
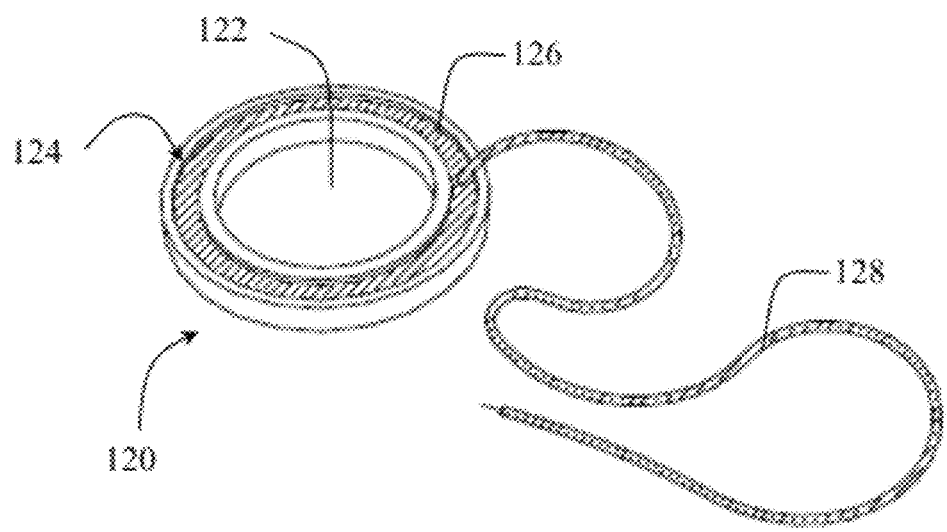
FIG. 2 is a perspective view of the ground ring.
Figure 3:
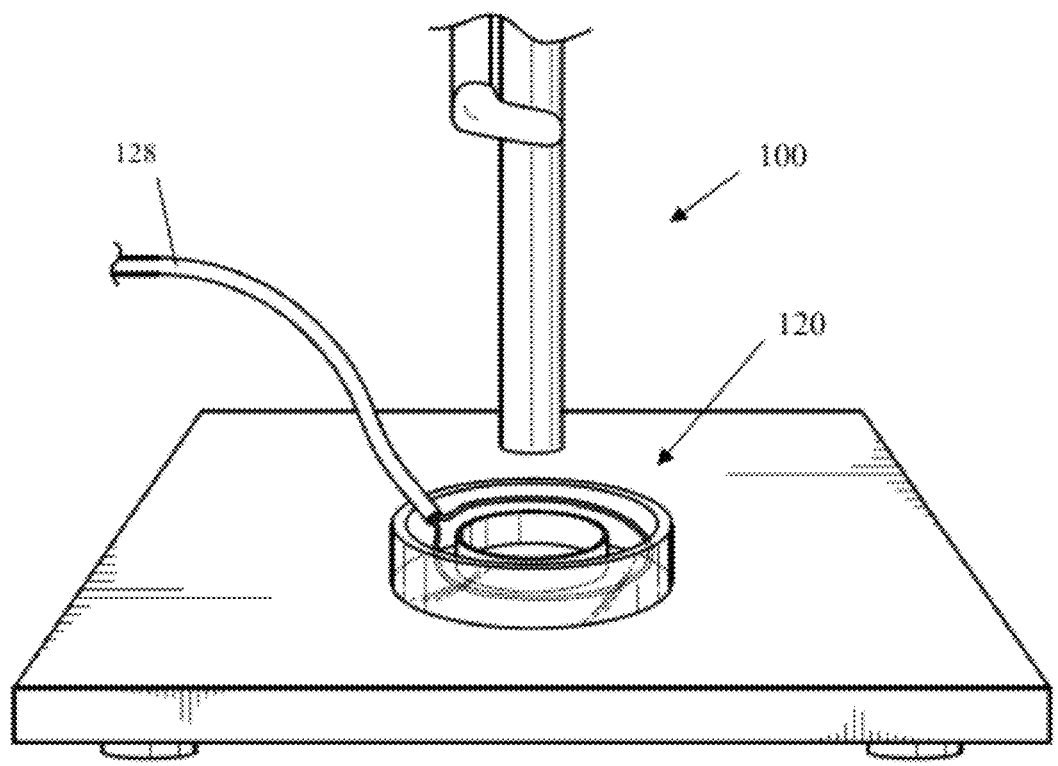
FIG. 3 is perspective view of the plasma pen and ground ring.

As shown in FIGS. 2 and 3, sample plate 120 is used in conjunction with electric field generation device 100. Sample plate 120 includes inner chamber 122 and outer chamber 124. Inner chamber 122 is adapted to hold a biological structure. Outer chamber 124 is adapted to receive grounding ring 126 which is connected to a ground through wire 128. Grounding ring 126 and wire 128 can be made from any conductive material as is known in the art. In another embodiment, wire 128 passes through high impedance. Grounding ring 126 can be placed directly on the surface of the biological structure. For example, for preventing hair growth, grounding ring 126 may be temporarily placed directly on the skin with a mild adhesive.

Figure 4:
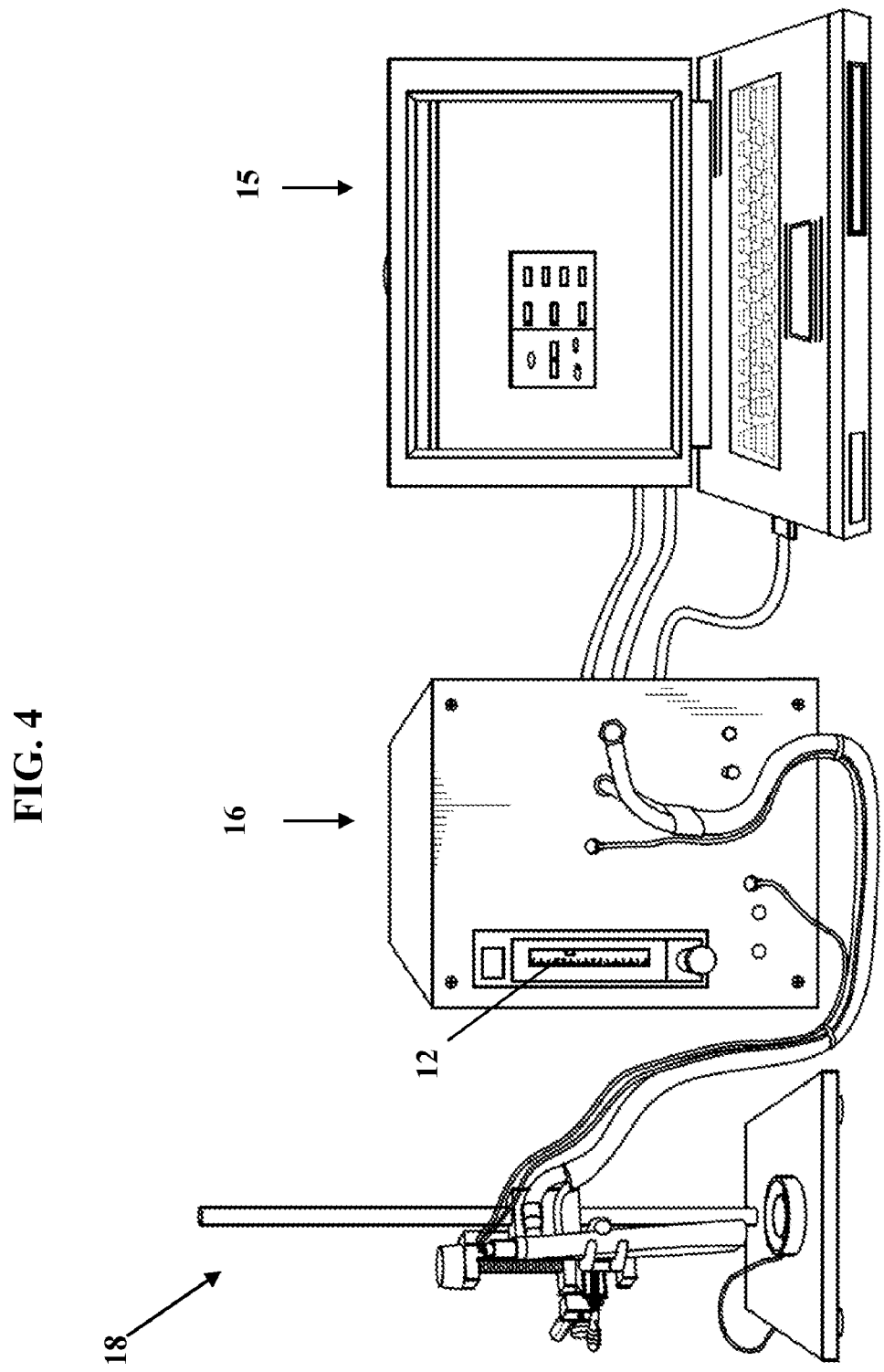
FIG. 4 is a perspective view of the plasma pen system.
Figure 5:
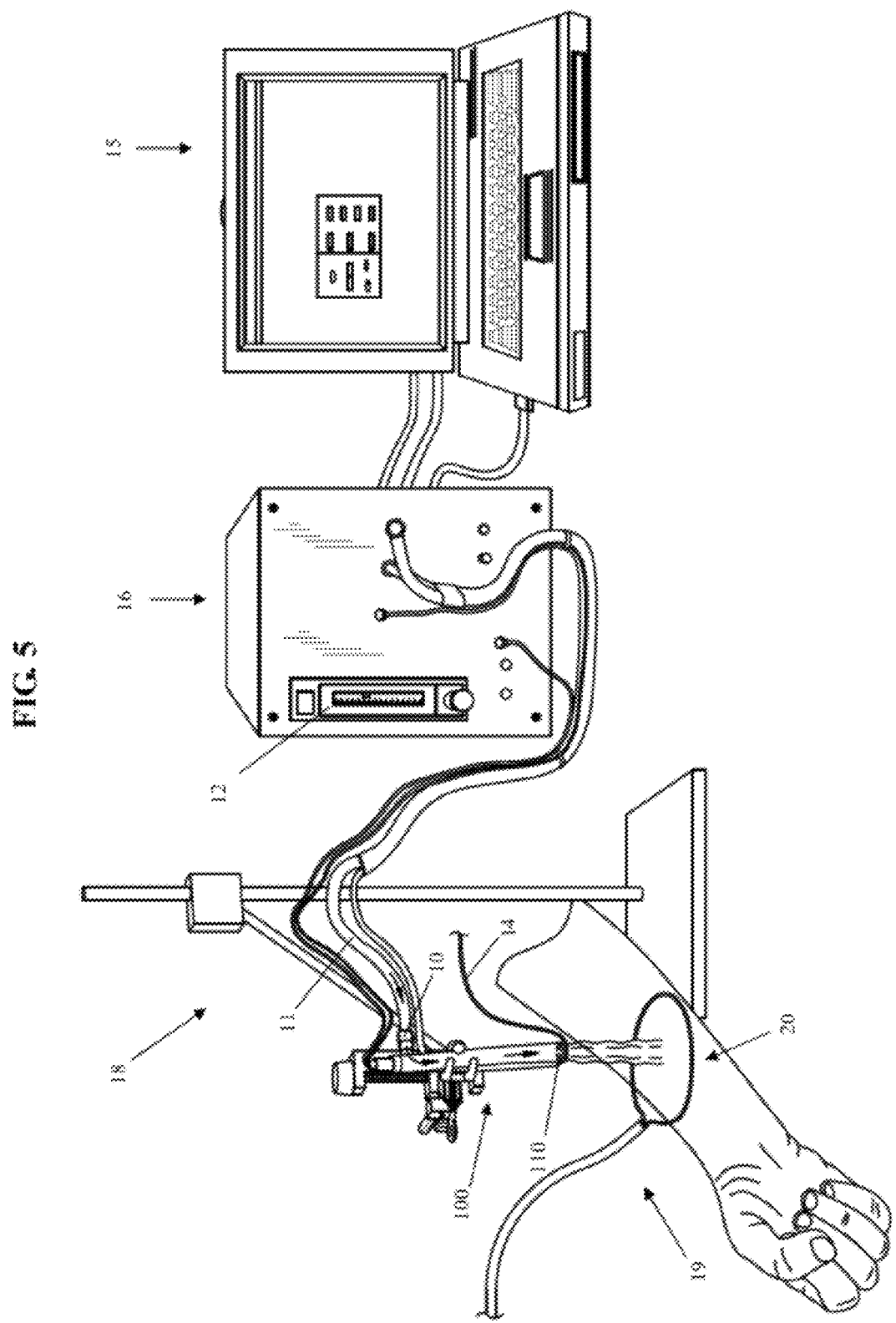
FIG. 5 is a perspective view of the plasma pen system as applied to a biological surface.

Device 100 is a hollow tube about the size of a pen, as depicted in FIGS. 4 and 5. A first end of tube 100 has gas inlet 10 that is connected to a gas source by flexible plastic hose 11. Gas hose 11 has inline flowmeter 12 used for precise control of the gas flow rate. A second end of tube 100, where gas escapes, houses annular electrode 110 (a stainless steel washer). Electrode 110 is connected to a high voltage low power supply through rubber jacketed wire 14 positioned along the outside of tube 100. The power supply is controlled remotely by computer interface program LabVIEW® 15. Interface 15 is used to control treatment time and to monitor voltage and current values leaving the high voltage generator. Interface 15 allows the user to set the experimental run time, operating voltage, and maximum current output. The power supply and computer interface are mounted in transportable metal box 16. Box 16 contains flowmeter 12, all electrical connections, and gas hose 11 connections. Tube 100 contains a pointing device (not shown) that allows the user to identify the center of plume of charges that are emitted from the device. In addition, the tube is mounted to manipulator stand 18 that allows the apparatus to be steadily positioned in four dimensions (x, y, z, and φ). The fourth dimension refers to an angular movement with respect to any of the x, y or z planes. Ground source 19 is positioned around treatment field 20 to prevent the buildup of charge on areas of the body that are not intended for treatment.

Originally, helium plasma work in tissues was initiated for the purpose of delivering DNA to the cells of skin and tumors. However, unexpected results occurred; particularly, the absence of hair growth that resulted in the skin that was treated with plasma.

The initial experimental evidence for this invention was obtained by treating 10 groups of female C57Bl/6 mice. Each mouse in the study had its left flank shaved prior to treatment. The treatment groups were as follows: no treatment, injection of DNA alone, 4 groups treated by Injecting of DNA followed by either 2, 5, 10, or 20 minutes of positive polarity plasma treatment, and 4 groups treated by injecting DNA followed by either 2, 5, 10, or 20 minutes of negative polarity plasma treatment. During the experiment, the plasma pen was maintained at a constant distance of 3 cm from the skin. All DNA was injected as a 50 microliter volume containing 100 micrograms of gWiz-Luc plasmid (encoding luciferase). All DNA injections were performed intradermally using a 25 gauge needle mounted on a 1 cc syringe. This study was originally designed to deliver DNA to the dermis. These experiments were successful and are part of another disclosure. However, during the 40 day follow up period to check for expression, it was observed that no hair regrew in animals that were treated with plasma of either polarity.

Figure 6:
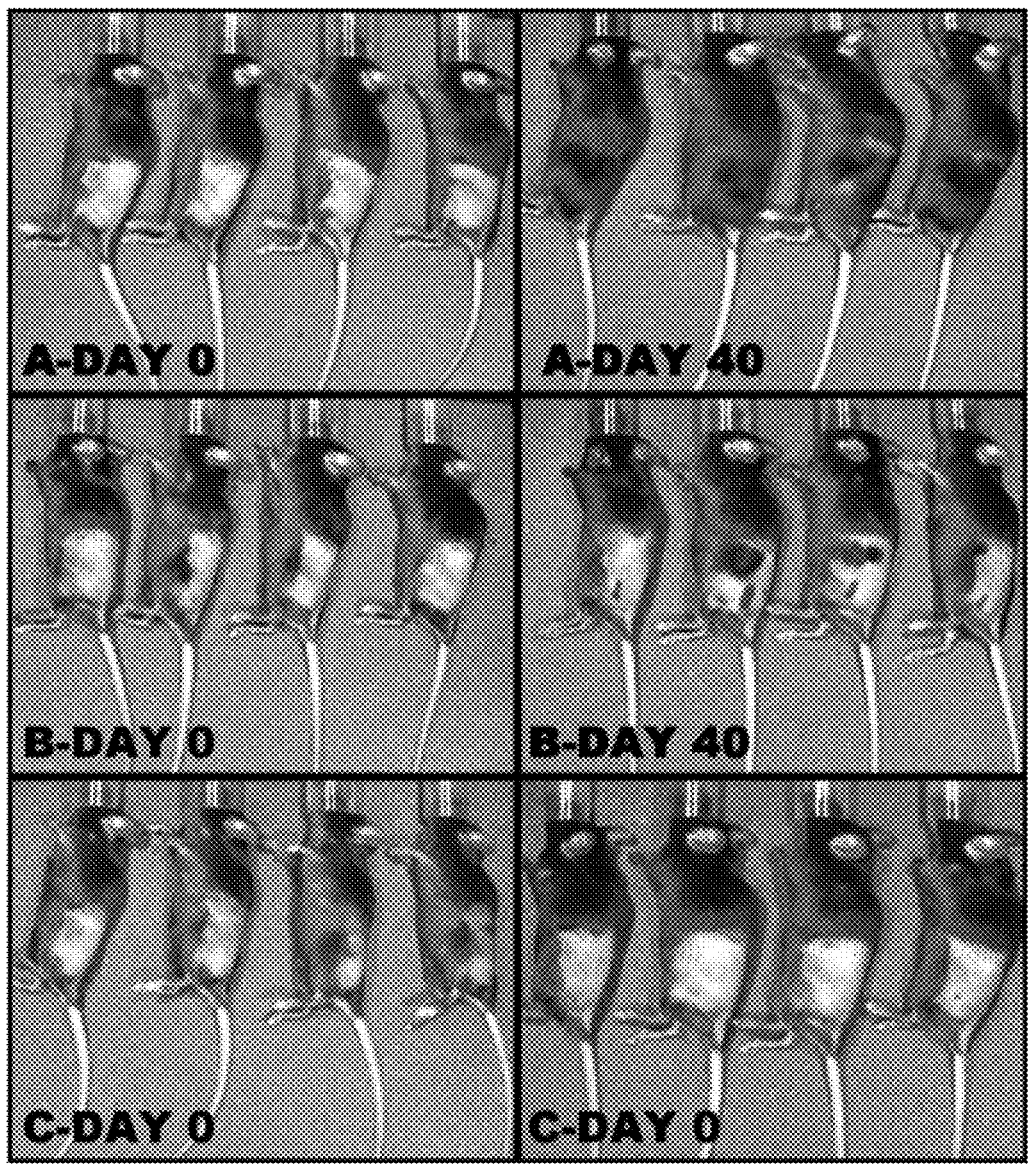
FIG. 6 shows photographs of animals treated with plasma.

FIG. 6 shows photographs of animals from three treatment groups on Day 0 (day of treatment) and Day 40 (termination of experiment). Animals that received no treatment are labeled as A, animals that received 20 minutes of positive plasma after DNA injection are labeled as B, and animals that received 20 minutes of negative plasma treatment after DNA injection are labeled as C. The shaved flanks of animals in the no treatment group (A—Day 0) compared to the total regrowth of hair in the same 4 animals at day 40 (A—Day 40). In contrast, animals that received 20 minutes of positive plasma treatment showed minimal hair regrowth from their shaved Day 0 state (B—Day 0) and the 40 day end point of the observation (B—Day 40). Similarly, the animals treated with negative plasma for 20 minutes showed a lack of hair regrowth over the 40 day follow up period (C—Day 0 versus C—Day 40). This data confirms that the absence of hair growth is a result of plasma treatment.

Figure 7:
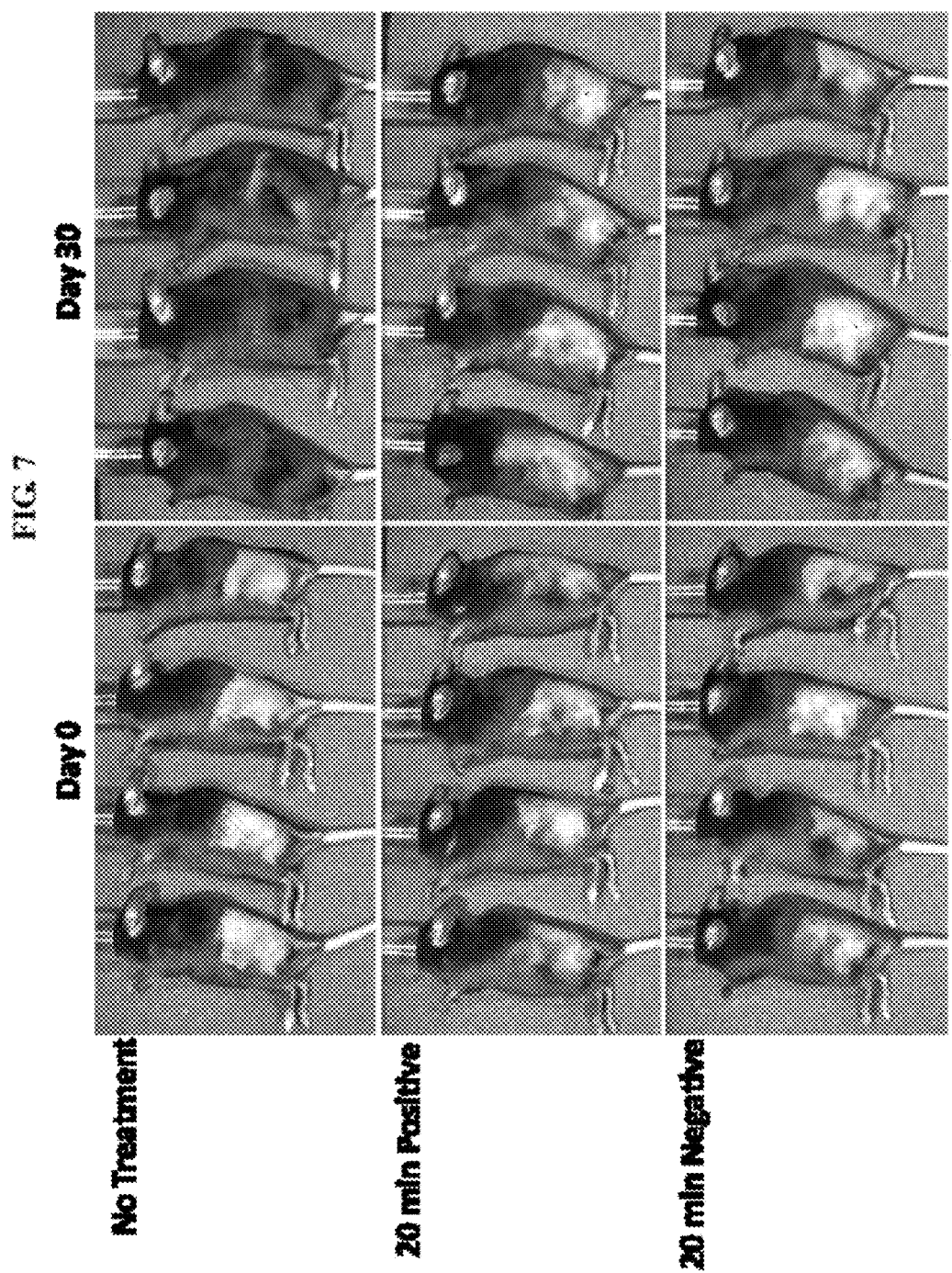
FIG. 7 shows photos of animals treated with plasma.

Following the initial unexpected results, additional experiments were conducted without injecting the mice with DNA. FIG. 7 shows photographic data of animals from three treatment groups on Day 0 (day of treatment) and Day 30 (termination of experiment). Animals that received no treatment are labeled as No Treatment. The other two treatment groups received either 20 minutes of positive plasma treatment or 20 minutes of negative plasma treatment. In contrast to the animals shown in FIG. 6, FIG. 7 animals did not have any DNA injected into their respective treatment sites. In each photo in FIG. 7, the same animals are shown on Day 0 and Day 30. The animals are shown in the same order, left to right, to facilitate comparison. All Day 0 data shows animals with shaved left flanks that received no treatment. On Day 30 the hair in the flanks of animals in the no treatment group was almost completely regrown. This growth occurred between day 21 and day 30. In contrast, animals that received either 20 minutes of positive plasma treatment or 20 minutes of negative plasma treatment showed minimal hair regrowth on Day 30.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

What is claimed is:

1. A method to cause hair loss or prevent or inhibit hair growth, comprising the steps of:
    providing an electric field generating device having at least one electrode capable of having a nonground potential applied to it;
    providing a gas source in fluid communication with the electrode;
    providing a biological structure;
    positioning the electric field generating device proximate to the biological structure;
    applying a first potential to the electrode;
    establishing a second potential by flowing the gas source past the electrode; and
    applying the second potential to the biological structure to prevent or inhibit hair growth.

2. The method to cause hair loss or prevent or inhibit hair growth of claim 1, further comprising the step of:
    providing a control means for controlling the flow of the gas source.

3. The method to cause hair loss or prevent or inhibit hair growth of claim 1, further comprising the step of:
    providing a means for controlling the run time, voltage, and current of the electrode.

4. The method to cause hair loss or prevent or inhibit hair growth of claim 1, further comprising the step of:
applying the second potential to the biological structure for the amount of time necessary to achieve the desired prevention of growth, or inhibition of growth.

5. The method to cause hair loss or prevent or inhibit hair growth of claim 4, further comprising the step of:
applying the second potential to the biological structure for 1 second to 2 hours.

6. The method to cause hair loss or prevent or inhibit hair growth of claim 1, further comprising the step of:
positioning the electric field generating device the desired distance from the biological structure.

7. The method to cause hair loss or prevent or inhibit hair growth of claim 6, further comprising the step of:
positioning the electric field generating device 0-20 cm from the biological structure.

8. The method to cause hair loss or prevent or inhibit hair growth of claim 1, further comprising the step of:
applying more than one potential simultaneously or in series to the biological structure.

9. The method to cause hair loss or prevent or inhibit hair growth of claim 1, further comprising the step of:
applying a conductive material that is grounded and in contact with the biological structure.

10. The method to cause hair loss or prevent or inhibit hair growth of claim 1, further comprising the step of:
applying a conductive material having a high impedance that is grounded and in contact with the biological structure.

11. The method to cause hair loss or prevent or inhibit hair growth of claim 1, further comprising the step of:
establishing a second potential by flowing the gas source past the electrode, whereby said second potential is positive plasma.

12. The method to cause hair loss or prevent or inhibit hair growth of claim 1, further comprising the step of:
establishing a second potential by flowing the gas source past the electrode, whereby said second potential is negative plasma.

13. The method to cause hair loss or prevent or inhibit hair growth of claim 1, further comprising the step of:
utilizing a corona charge, DC plasma, AC plasma, RF plasma, plasma formed from any gas including air, plasma formed from any mixture of two or more gasses, or electrospray technology as said second potential.

14. An apparatus to cause hair loss or prevent or inhibit hair growth, comprising:
a hollow body having a first and a second end;
a gas source in fluid communication with the first end of the hollow body, said gas source supplying a flow of gas through the hollow body;
an electrode secured to the second end of the hollow body, said electrode connected to a power supply thereby creating an electric field to ionize the gas wherein the electric field is created using constant direct current (DC) voltage; and
a conductive material surrounding a treatment site on the biological structure and connected to ground by a wire wherein the conductive material is in electrical contact with the biological structure.

15. An apparatus to cause hair loss or prevent or inhibit hair growth in claim 14, further comprising:
a pointing device secured to said hollow body for accurate targeting and positioning.

16. An apparatus to cause hair loss or prevent or inhibit hair growth in claim 14, wherein the conductive material is a grounding ring that is positioned around a treatment site on the biological structure.

17. An apparatus to cause hair loss or prevent or inhibit hair growth in claim 14, wherein the wire passes through a high impedance.

18. An apparatus to cause hair loss or prevent or inhibit hair growth in claim 14, further comprising:
a means for controlling and monitoring the run time, voltage, and current of the electrode.

19. An apparatus to cause hair loss or prevent or inhibit hair growth in claim 14, further comprising:
a means for controlling and monitoring the flow of the gas.

20. An apparatus to cause hair loss or prevent or inhibit hair growth in claim 14, further comprising:
said apparatus mounted to a manipulator stand that allows the apparatus to be moved in any direction.

* * * * *